United States Patent [19]

Simon et al.

[11] Patent Number: 4,897,254

[45] Date of Patent: Jan. 30, 1990

[54] RADIOACTIVE COMPOSITIONS FOR THE TREATMENT OF CALCIFIC TUMORS

[75] Inventors: Jaime Simon, Angleton, Tex.; Wynn A. Volkert, Columbia, Mo.; David A. Wilson, Richwood, Tex.; David E. Troutner, Columbia, Mo.; William F. Goeckeler, Midland, Mich.

[73] Assignee: The Dow Chemical Company, Midland, Mich.

[21] Appl. No.: 21,382

[22] Filed: Mar. 3, 1987

Related U.S. Application Data

[63] Continuation-in-part of Ser. No. 762,361, Aug. 5, 1985, abandoned, which is a continuation-in-part of Ser. No. 652,702, Sep. 21, 1984, abandoned.

[51] Int. Cl.$^4$ .................... A61K 43/00; C07F 11/00
[52] U.S. Cl. ........................................ 424/1.1; 534/10
[58] Field of Search ............................ 424/1.1; 534/10

[56] References Cited

U.S. PATENT DOCUMENTS

| | | | |
|---|---|---|---|
| 3,965,254 | 6/1976 | Tofe et al. | 424/1.1 |
| 4,017,596 | 4/1977 | Loberg et al. | 424/1.1 |
| 4,088,747 | 5/1978 | Hunt et al. | 424/1.1 |
| 4,091,088 | 5/1978 | Hunt et al. | 424/1.1 |
| 4,308,249 | 12/1981 | Frank et al. | 424/1.1 |
| 4,352,751 | 10/1982 | Wieder et al. | 424/1.1 |
| 4,399,817 | 8/1983 | Benedict | 424/1.1 |
| 4,560,548 | 12/1985 | Simon et al. | 424/1.1 |
| 4,606,907 | 8/1986 | Simon et al. | 424/1.1 |
| 4,647,447 | 3/1987 | Gries et al. | 424/1.1 |

FOREIGN PATENT DOCUMENTS 83129  7/1983  European Pat. Off. .

OTHER PUBLICATIONS

Journ. Nucl. Med., vol. 1 (1960) pp. 1–13.
Journ. Nucl. Med., vol. 10 (1969) pp. 49–51, O'Mara et al.
Int. J. Clin. Pharmacol., 9, 3 (1974) pp. 199–205.
Journal of Urology, vol. 116 (1976) pp. 764–768.
Seminars in Nucl. Med., vol. IX, No. 2, (Apr. 1979) pp. 114–120.
19th Int. Annual Meeting Soc. Nucl. Med. Europe, Bern Switzerland, 9-8/11–81.
Journ. Nucl. Med., vol. 24 (1983) p. P-125.
Journ. Nucl. Med., vol. 25 (1984) pp. 1356–1361.
Journ. Nucl. Med., vol. 25 (1984) p. P-129.
Int. J. Applied Rad. & Isotopes, Mathisu, L. et al., vol. 30, pp. 725–727 (1979).
Int. J. of Applied Radiation & Isotopes, vol. 14, pp. 129–135 (1963) Rosoff et al.
Technical Report from the Medical Dept., Brookhaven Nat. Lab. (BNL–24614).
Chemical Abstract 70:100130f.
Chemical Abstract 76:37422j.
Chemical Abstract 84:129901h.
Chemical Abstract 912:97498h.
Gilyazutdinou et al., CA82:108229p (1975).
Thakur et al., CA100:180971g (1984).

*Primary Examiner*—Howard J. Locker
*Assistant Examiner*—J. E. Thomas

[57] ABSTRACT

Certain particle-emitting radionuclides, e.g. Samarium-153, have been complexed with certain alkylenepolyaminocarboxylic acid chelants. Compositions containing these complexes have been found useful in the treatment of calcific tumors in animals. The stability constant, log K, of the useful complexes is from about 14 to about 17 and the molar ratio of chelant to radionuclide in the compositions is such that the chelant is present in an amount sufficient to inhibit uptake of the radionuclide by soft tissue.

18 Claims, No Drawings

RADIOACTIVE COMPOSITIONS FOR THE TREATMENT OF CALCIFIC TUMORS

CROSS-REFERENCE TO RELATED APPLICATION

This application is a continuation-in-part of our co-pending application Ser. No. 762,361, filed Aug. 5, 1985 now abandoned which is a continuation-in-part of Ser. No. 652,702, now abandoned filed Sept. 21, 1984, now abandoned.

BACKGROUND OF THE INVENTION

The development of bone metastases is a common and often catastrophic event for a cancer patient. The pain, pathological fractures, frequent neurological deficits and forced immobility caused by these metastatic lesions significantly decrease the quality of life for the cancer patient. The number of patients that contract metastatic disease is large since nearly 50% of all patients who contract breast, lung or prostate carcinoma will eventually develop bone metastases. Bone metastases are also seen in patients with carcinoma of the kidney, thyroid, bladder, cervix and other tumors, but collectively, these represent less than 20% of patients who develop bone metastases. Metastatic bone cancer is rarely life threatening and occasionally patients live for years following the discovery of the bone lesions. Initially, treatment goals center on relieving pain, reducing requirements for narocotic medication and increasing ambulation. Clearly, it is hoped that some of the cancers can be cured.

The use of radionuclides for treatment of cancer metastatic to the bone dates back to the early 1950's. It has been proposed to inject a radioactive particle-emitting nuclide in a suitable form for the treatment of calcific lesions. It is desirable that such nuclides be concentrated in the area of the bone lesion with minimal amounts reaching the soft tissue and normal bone. Radioactive phosphorus (P-32 and P-33) compounds have been proposed, but the nuclear and biolocalization properties limit the utility of these compounds. (Kaplan, E., et al, *Journal of Nuclear Medicine*, Vol. 1, No. 1, page 1, 1960); (U.S. Pat. No. 3,965,254).

Another attempt to treat bone cancer has been made using phosphorus compounds containing a boron residue. The compounds were injected into the body (intravenously) and accumulated in the skeletal system. The treatment area was then irradiated with neutrons in order to activate the boron and give a therapeutic radiation dose. (U.S. Pat. No. 4,399,817).

In the above mentioned procedures, it is not possible to give therapeutic doses to the tumor without substantial damage to normal tissues. In many cases, especially for metastatic bone lesions, the tumor has spread throughout the skeletal system and amputation or irradiation is not practical. (*Seminars in Nuclear Medicine*, Vol. IX, No. 2, Apr., 1979).

The use of Re-186 complexed with a diphosphonate has also been proposed. (Mathieu, L. et al, *Int. J. Applied Rad. & Isotopes*, Vol. 30, pp. 725-727, 1979; Weinenger, J., Ketring, A. R., et al, *Journal of Nuclear Medicine*, Vol. 24, No. 5, P125, 1983). However, the preparation and purification needed for this complex limits its utility and wide application.

Strontium-89 has also been proposed for patients with metastic bone lesions. However, the long half-life (50.4 days), high blood levels and low lesion to normal bone ratios can be disadvantageous. (Firusian, N., Mellin, P., Schmidt, C. G., *The Journal of Urology*, Vol. 116, page 764, 1976; Schmidt, C. G., Firusian, N., *Int. J. Clin. Pharmacol.*, 93:199-205, 1974).

A palliative treatment of bone metastases has been reported which employed I-131 labelled α-amino-(3-iodo-4-hydroxybenzylidene)diphosphonate (Eisenhut, M., *Journal of Nuclear Medicine*, Vol. 25, No. 12, pp. 1356-1361, 1984). The use of radioiodine as a therapeutic radionuclide is less than desirable due to the well known tendency of iodine to localize in the thyroid. Eisenhut lists iodide as one of the possible metabolites of this compound. In addition, any I-131 left over from the iodination reaction and not separated in the washing procedure also constitutes a threat to the thyroid.

Aminocarboxylic acids are known to chelate metal ions. Particularly stable chelates are formed with metals from the alkaline earth and transition metal series.

O'Mara et al (*Journal of Nuclear Medicine*, 10, pp. 49-51, 1969) have prepared rare earth complexes of aminocarboxylic acids at chelant to metal ratios of 10/1. They find good skeletal properties and propose their use as diagnostic skeletal agents. In addition to high bone uptake, high amounts of radiation were observed in muscle and/or liver. Of the rare earth nuclides evaluated Sm-153 and Er-171 were indicated as having the most suitable characteristics for imaging in humans. The utility of these agents for therapy, however, is not suggested.

Rosoff, B. et al., *International Journal of Applied Radiation and Isotopes*, Vol. 14, pp. 129-135 (1963), disclose complexes of EDTA (ethylenediaminetetra(acetic acid)) and NTA (nitrilotri(acetic acid)) with certain radionuclides, namely Sc-46, Y-91, La-140 and Sm-153. The relationship of the stability constant of these complexes to urinary excretion is shown. Chelant to metal molar ratios of 5/1 were employed and high concentrations of radioactivity were observed in the liver, spleen, kidney, lung and bone.

It has now been discovered that certain particle-emitting radionuclides complexed with certain alkylenepolyaminocarboxylic acids can be effectively used in compositions useful as therapeutic agents in the treatment of bone cancer.

SUMMARY OF THE INVENTION

Certain particle-emitting radionuclides, e.g. Samarium-153, have been complexed with certain alkylenepolyaminocarboxylic acid chelants. Compositions containing these radionuclide-chelant complexes show promise in the treatment of calcific tumors in animals.

The compositions containing the radionuclide-chelant complexes operable in the invention are those in which the alkylenepolyaminocarboxylic acid complex of the radionuclide has a stability constant, expressed as log K, of from about 14 to about 17 and wherein the complexed radionuclide is employed in the presence of an excess of a complexing ligand, i.e., the alkylenepolyaminocarboxylic acid chelant.

DETAILED DESCRIPTION OF THE INVENTION

Therapeutically useful or effective compositions according to the present invention must, insofar as possible, fit certain criteria. While there are many alkylenepolyaminocarboxylic acids, only a relative few can be combined with desired radionuclides so that the resulting composition is therapeutically effective. While the properties of the radionuclide are important, the overall properties of the composition containing the radionuclide-chelant complex is the determining factor. The disadvantages of any one property may be overcome by the superiority of one or more of the properties of either ligand or radionuclide and their combination, as employed in the composition must be considered in toto.

The following is a discussion of those criteria which must be considered in choosing any particular combination (i.e., complex) or radionuclide and alkylenepolyaminocarboxylic acid ligand employed in the compositions of the invention. Radionuclide-chelant complexes, when used in the absence of an appropriate excess of the ligands employed in the invention may not be therapeutically useful or effective.

There is a need, therefore, for compositions possessing the following criteria by which it is possible to deliver therapeutic radiation doses to calcific tumors with minimal doses to soft tissue.

The radionuclide must be delivered preferentially to the bone rather than to soft tissue. Most particularly, uptake in either liver or bone marrow is undesirable.

Another important criterion is the ratio of the amount of radionuclide taken up by the cancerous bone to that taken up by normal bone. High ratios are preferred.

The radionuclide should be cleared rapidly from non-osseous tissue to avoid unnecessary damage to such tissues, e.g., it should clear rapidly from the blood.

The proposed use for the compositions of this invention is the therapeutic treatment of calcific tumors in animals. As used herein, the term "animals" includes humans; the term "calcific tumors" includes primary tumors, where the skeletal system is the first site of involvement, and metastatic bone cancer where the neoplasm spreads from other primary sites, such as prostate and breast, into the skeletal system. This invention provides a means of alleviating pain and/or reducing the size of, and/or inhibiting the growth and/or spread of, or causing regression of and/or destroying the calcific tumors by delivering a therapeutic radiation dose.

The composition may be administered as a single dose or as multiple doses over a longer period of time. Delivery of the radionuclide to the tumor must be in sufficient amounts to provide the benefits referred to above.

The organic carboxylic acid derivatives, i.e., the ligands, which have been found useful in complexing the particle-emitting radionuclides are alkylenepolyamino compounds wherein at least one amine hydrogen is replaced by a carboxyalkyl* radical.
*Method of making carboxyalkylamines is disclosed in *Chelating Agents and Metal Chelates*, Ed. F. P. Dwyer, D. P. Mellor, Academic Press, NY (1964), pp. 285–286.

The particle-emitting radionuclides, Samarium-153 (Sm-153), Ytterbium-175 (Yb-175), Lutetium-177 (Lu-177), Gadolinium-159 (Gd-159), and Holmium-166 (Ho-166) have been complexed with certain alkylenepolyaminocarboxylic acids. We have now found that those alkylenepolyaminocarboxylic acid complexes with radionuclides possessing Log K** values of from about 14 to about 17 fit the aforementioned criteria. For example, Sm-153-nitrilotriacetic acid (Sm-153-NTA), Log K=11.3, has a high liver uptake and is thus unsuitable for therapeutic use. Furthermore, Sm-153-diethylenetriaminepentaacetic acid (Sm-153-DTPA), Log K=22.3, has low skeletal uptake and thus is also considered to be unacceptable for use. Non-limiting examples of appropriate alkylenepolyaminocarboxylic acids and their Log K values may be found in Martel, A. E. and Smith, R. M., *Critical Stability Constants*, Vol. 1, Plenum Press, N.Y. and London (1974), and Sillén, L. G. and Martel, A. E., *Stability Constants of MetalIon Complexes*, Supplement Nos. 17 and 25, The Chemical Society, Burlington House, London (1964; 1977). Representative examples of alkylenepolyaminocarboxylic acids which are useful in preparing the complexes employed in this invention are hydroxyethylethylenediaminetriacetic acid (HEEDTA) and ethylenediaminetetraacetic acid (EDTA).

**K is an equilibrium constant defined by $[M \cdot L]/[M] \times [L]$ wherein the bracketed letters represent concentrations of metal (M), ligand (L) and complex (M·L). For chelation reactions this constant is called the stability constant and is a measure of the affinity of the complexing agent for a particular metal. Since protons compete with metal ions for the ligand, the stability constant is pH dependent. To describe the reaction at a specific pH, conditional stability constants can be calculated. (See Fritz, J. S. and Schenk, G. H., *Quantitative Analytical Chemistry*, Allyn and Bacon, Inc., Boston (1973)

For the purpose of the present invention, therapeutically effective compositions described herein and physiologically acceptable salts thereof are considered equivalent. Physiologically acceptable salts refer to the acid addition salts of those bases which will form a salt with at least one acid group of the ligand, or ligands, employed in the composition and which will not cause an adverse physiological effect when administered to an animal at dosages consistent with good pharmacological practices. Suitable bases include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like; ammonia, primary, secondary and tertiary amines and the like. Physiologically acceptable salts may be prepared by treating with an appropriate base.

Radionuclides can be produced in several ways. In a reactor, a nuclide is bombarded with neutrons to obtain a nuclide with additional neutrons in its nucleus.

e.g. Sm-152+neutron→Sm-153+gamma

Another method of obtaining radionuclides is by bombarding nuclides with particles in a linear accelerator or cyclotron. Yet another way of obtaining radionuclides is to isolate them from fission product mixtures. The method of obtaining the radionuclide is not critical to the present invention.

The samarium used in the following examples was either natural $Sm_2O_3$ (99.9 percent from Spex Industries) or isotopically enriched (99.06 percent Sm-152) $Sm_2O_3$.

The Sm-153 used in this study was produced by neutron irradiation at the University of Missouri Research Reactor. Preliminary studies were carried out using Sm-153 produced by short (5–30 minutes) irradiations of natural $Sm_2O_3$, in the reactor's pneumatic tube system. The specific activity of Sm-153 produced by this method was 0.5–3.0 Ci/g (18.5 to 111 GBq/g).

The majority of this work was carried out using Sm-153 produced by irradiating 99.06 percent enriched $^{152}Sm_2O_3$ in the first row reflector of the reactor. Irradiations were generally carried out for 50–60 hours, yielding a Sm-153 specific activity of 1000–1300 Ci/g ($37 \times 10^3$ to $48.1 \times 10^3$ GBq/g).

To irradiate $Sm_2O_3$ for production of Sm-153, the desired amount of target was first weighed into a quartz vial, the vial flame sealed under vacuum and welded into an aluminum can. The can was irradiated for the desired length of time, cooled for several hours and opened remotely in a hot cell. The quartz vial was removed and transferred to a glove box, crushed into a glass vial which was then sealed with a rubber septum and an aluminum crimp cap. One milliliter of 1–4M HCl was then added to the vial via syringe to dissolve the $Sm_2O_3$. Once dissolved, the solution was diluted to the appropriate volume by addition of water. The solution was removed from the original dissolution vial which contains the chards of the crushed quartz vial, and transferred via syringe to a clean glass serum vial. Similar procedures were used to prepare the other radionuclides, i.e. Lu-177, Yb-175, Gd-159 and Ho-166.

When aqueous solutions of metal ions are mixed with solutions containing complexing agents, such as those described in this invention, a complex between the metal ion and the ligand can be formed as shown by the equation below.

$$M + L \rightleftharpoons M \cdot L$$

The reaction is believed to be an equilibrium such that the concentrations of radionuclide, or metal (M), and complexing agent, or ligand (L), can affect the concentration of species present in solution. The equilibrium constant K (previously defined) is a mathematical expression that relates the concentrations of the reactants and reaction products involved in any equilibrium reaction. For chelation reactions this constant is called the stability constant and is a measure of the affinity of the complexing agent for a particular metal.

Competing side reactions, such as metal hydroxide formation, can also occur in aqueous solution.

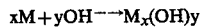

$$xM + yOH^- \rightarrow M_x(OH)_y$$

The $OH^-$ concentration in solution which is related to pH is, therefore, an important parameter. If the pH is too high, the metal tends to form metal hydroxides rather than complexes. The complexing agents may also be affected by low pH. Complexation may require the loss of proton(s); therefore at low pH, conditions may not be favorable for complexation to occur. The complexes of this invention can be formed within a certain pH range. Consideration must be given to the solubility characteristics of the ligand, radionuclide, and complex. Although complexation will occur at other pH values, a pH of from about 5–11 is preferred for complexation.

The metal and ligand may be combined under any conditions which allow the two to form a complex. Generally, mixing in water at a controlled pH (the choice of pH is dependent upon the choice of ligand and radionuclide) is all that is required.

In the practice of the invention, it is necessary to employ the comlexed nuclide in the presence of an excess of ligand. Such excess should provide an amount sufficient to inhibit significant uptake of the radionuclide by soft tissue. The excess ligand may be the same as or different from that used to complex the radionuclide. Although it is difficult to generalize, it is believed that the molar ratio of ligand or chelant to metal or radionuclide, i.e., L/M, in the composition is desirably about 50:1 or more. The preferred ratio will depend upon the particular radionuclide and ligand selected. While L/M molar ratios of less than about 50:1 may in some cases be useful, it is desirable for the welfare and safety of the patient to use the higher ratios in order to minimize the amounts of radionuclide present in blood, liver, muscle and other organs.

The various compositions employed in this invention were prepared by placing the desired amount of ligand in a vial and dissolving the ligand by addition of water. At some higher ligand concentrations, it was necessary to add base in order to completely dissolve the ligand. Heating was also found to be useful for dissolving the ligands. The appropriate amount of the Sm-153 or other radionuclides in the stock solution described above was then added to the ligand solution. The pH of the resulting solution was then raised to the appropriate level, preferably 7–8, by addition of NaOH.

The invention described herein provides a means of delivering a therapeutic radiation dose to calcific tumors. However, it may also be desirable in the cases where the radionuclide has imageable gamma photons to administer a "sub-therapeutic" dose to determine the fate of the radionuclide using a scintillation camera prior to administering a therapeutic dose. Therapeutic doses will be administered in sufficient amounts to alleviate pain and/or inhibit tumor growth and/or cause regression of the tumor and/or destroy the tumor. Amounts of radionuclide needed to provide the desired therapeutic dose will be determined experimentally and optimized for each particular composition. The amount of activity required to deliver a therapeutic dose will vary with the individual composition employed. The composition to be administered may be given in a single treatment or fractionated into several portions and administered at different times. Administering the composition in fractionated doses may make it possible to minimize damage to non-target tissue. Such multiple dose administration may be more effective.

It may be possible to achieve the same beneficial results of high delivery of the radionuclide to the area of the tumor, but with little soft tissue damage, by administering the ligand and the radionuclide in a manner which allows formation of the radionuclide-chelant comlex in situ such as by simultaneous or near simultaneous administration of the radionuclide and an appropriate excess of the ligand or by the administration of the ligand and a radionuclide complexed with a weaker ligand, i.e., one which undergoes ligand exchange with ethylenediamine tetraacetic acid or hydroxyethylethylenediaminetriacetic acid, such that the desired radionuclidechelant complex (those having a log of the stability constant of the radionuclide with the liquid of about 14 to about 17) is formed via ligand exchange in situ.

Studies to determine the qualitative distribution of the various radionuclides were conducted by injecting the compositions into rats and obtaining the gamma ray images of the entire animal at various times up to two hours after injection.

Quantitative biodistributions were obtained by injecting 50–100 microliters of the composition into the tail vein of unanesthetized male Sprague Dawley rats. The rats were then placed in cages lined with absorbent paper in order to collect all urine excreted prior to sacrifice. After a given period of time, the rats were sacrificed by cervical dislocation and the various tissues dissected. The samples were then rinsed with saline, blotted dry on absorbent paper and weighed. The radiation in the samples was measured with a NaI scintillation counter.

The following examples are illustrative of the present invention and are not to be construed as limiting the scope thereof.

EXAMPLE 1

A quantity of 25 to 35 milligrams of N-hydroxyethylethylenediaminetriacetic acid (HEEDTA) was weighed into a vial and dissolved using 0.75 ml of distilled water. To this, 0.25 ml of Sm-153 (~10 mCi) in dilute HCl was added. The pH of the resulting solution was then adjusted to 10 by addition of NaOH. The resulting solution was heated to 60° C.-70° C. for 30 minutes in a water bath. The pH of the solution was then adjusted to 7-8 by addition of HCl. The molar ratio of L/M was 300/1. Log K of the complex of Sm-153-HEEDTA is 15.4.

A laboratory rat was injected with the above composition (50-100 μl) via the tail vein. After 2 hours, the animal was sacrificed by cervical dislocation and organs and tissues removed. Samples were counted with a NaI scintillation counter to determine the biolocalization of the radinuclide. It was found that a significant amount (50-60 percent) of the activity was concentrated in the skeletal system with very little soft tissue uptake. Most of the activity not found in the skeleton was cleared through the kidneys into the urine. Scintillation scans of animals treated in the same manner showed the activity concentrating in the skeletal system.

EXAMPLE 2

A quantity of 25 to 35 milligrams of N-hydroxyethylethylenediaminetriacetic acid (HEEDTA) was weighed into a vial and dissolved using 0.75 ml of distilled water. To this, 0.25 ml of Gd-159 (~10 mCi) in dilute HCl was added. The pH of the resulting solution was then adjusted to 10 by addition of NaOH. The resulting solution was heated to 60° C.-70° C. for 30 minutes in a water bath. The pH of the solution was then adjusted to 7-8 by addition of HCl. The molar ratio L/M was 300/1. The log K of the complex of Gd-159-HEEDTA is 15.3.

Laboratory rats were injected with the above composition (50-100 μl) via the tail vein. After 2 hours, the animals were sacrificed by cervical dislocation and organs and tissues removed. Samples were counted with a NaI scintillation counter to determine the biolocalization of the radionuclide. It was found that a significant amount (40-50 percent) of the activity was concentrated in the skeletal system with very little soft tissue uptake. Most of the activity not found in the skeleton was cleared through the kidneys into the urine. Scintillation scans of animals treated in the same manner showed the activity concentrating in the skeletal system.

EXAMPLE 3

A quantity of 25 to 35 milligrams of N-hydroxyethylethylenediaminetriacetic acid (HEEDTA) was weighed into a vial and dissolved using 0.75 ml of distilled water. To this, 0.25 ml of Yb-175 (~10 mCi) in dilute HCl was added. The pH of the resulting solution was then adjusted to 10 by addition of NaOH. The resulting solution was heated to 60° C.-70° C. for 30 minutes in a water bath. The pH of the solution was then adjusted to 7-8 by addition of HCl. The molar ratio of L/M was 300/1. The log K of the complex of Yb-175-HEEDTA is 16.0.

Laboratory rats were injected with the above composition (50-100μl) via the tail vein. After 2 hours, the animals were sacrificed by cervical dislocation and organs and tissues removed. Samples were counted with a NaI scintillation counter to determine the biolocalization of the radionuclide. It was found that a significant amount (20-30 percent) of the activity was concentrated in the skeletal system with very little soft tissue uptake. Most of the activity not found in the skeleton was cleared through the kidneys into the urine. Scintillation scans of animals treated in the same manner showed the activity concentrating in the skeletal system.

EXAMPLE 4

A quantity of 25 to 35 milligrams of N-hydroxyethylethylenediaminetriacetic acid (HEEDTA) was weighed into a vial and dissolved using 0.75 ml of distilled water. To this, 0.25 ml of Lu-177 (~10mCi) in dilute HCl was added. The pH of the resulting solution was then adjusted to 10 by addition of NaOH. The resulting solution was heated to 60° C.-70° C. for 30 minutes in a water bath. The pH of the solution was then adjusted to 7-8 by addition of HCl. The molar ratio of L/M was 300/1. The log K of the complex of Lu-177-HEEDTA is 16.0.

Laboratory rats were injected with the above composition (50-100 μl) via the tail vein. After 2 hours, the animals were sacrificed by cervical dislocation and organs and tissues removed. Samples were counted with a NaI scintillation counter to determine the biolocalization of the radionuclide. It was found that a significant amount (20-30 percent) of the activity was concentrated inthe skeletal system with very little soft tissue uptake. Most of the activity not found in the skeleton was cleared through the kidneys into the urine. Scintillation scans of animals treated in the same manner showed the activity concentrating in the skeletal system.

EXAMPLE 5

A quantity of 25 to 35 milligrams of disodium dihydrogen ethylenediaminetetraacetic acid dihydrate (Na)$_2$EDTA·2H$_2$O was weighed into a vial and dissolved using 0.75 ml of distilled water. To this, 0.25 ml of Sm-153 (~10 mCi) in dilute HCl was added. The pH of the resulting solution was then adjusted to 10 by addition of NaOH. The resulting solution was heated to 60° C.-70° C. for 30 minutes in a water bath. The pH of the solution was then adjusted to 7-8 by addition of HCl. The molar ratio of L/M was 300/1. The log K of the complex of Sm-153-EDTA is 17.1.

Laboratory rats were injected with the above composition (50-100 μl) via the tail vein. After 2 hours, the animals were sacrificed by cervical dislocation and organs and tissues removed. Samples were counted with a NaI scintillation counter to determine the biolocalization of the radionuclide. It was found that a significant amount (40-50 percent) of the activity was concentrated in the skeletal system with very little soft tissue uptake. Most of the activity not found in the skeleton was cleared through the kidneys into the urine. Scintillation scans of animals treated in the same manner showed the activity concentrating in the skeletal system.

EXAMPLE 6

In the manner of the preceding examples HEEDTA was complexed with Hl-166 at a ligand to radionuclide ratio of 300 to 1 and injected in laboratory rats in the same amounts. The log K of the complex of Ho-166-HEEDTA is 15.4.

The two-hour rat biodistribution data for the radionuclide used in the compositions of Examples 1–6 are given in Table I. The numbers given for each example represent the percentage of the administered dose which localized in the indicated tissue. The ratios of amounts of radiation observed in bone relative to other organs were calculated based on the % dose/g in the bone and the particular organ.

TABLE I

|  | EXAMPLE | | | | | |
| --- | --- | --- | --- | --- | --- | --- |
|  | 1 | 2 | 3 | 4 | 5 | 6 |
|  | Sm-153 | Gd-159 | Yb-175 | Lu-177 | Sm-153 | Ho-166 |
| Tissue | HEEDTA | HEEDTA | HEEDTA | HEEDTA | EDTA | HEEDTA |
| Bone | 58 | 44 | 25 | 21 | 43 | 66 |
| Blood | 0.18 | 0.13 | 0.33 | 0.40 | 0.38 | 0.11 |
| Liver | 2.42 | 0.73 | 0.36 | 2.62 | 4.4 | 0.35 |
| Bone/Blood | 245 | 297 | 64 | 50 | 84 | 502 |
| Bone/Muscle | 426 | 649 | 199 | 97 | 184 | 189 |

Comparataive Examples A and B

Compositions containing complexes of (A) nitrilotriacetic acid (NTA) with Sm-153, having a log K of 11.3, and (B) diethyleneriaminepentaacetic acid (DTPA), having a log K of 22.3, were tested in the manner of Example 1. The L/M molar ratio in each composition was 300/1. Results are given in Table II.

TABLE II

| Tissue | Example A | Example B |
| --- | --- | --- |
| Bone | 49 | 0.19 |
| Blood | 0.64 | 0.19 |
| Liver | 8.6 | 0.29 |
| Bone/Blood | 86 | 0.8 |
| Bone/Muscle | 171 | 1.0 |

It should be noted that the comparative examples have certain undesirable properties which make them inferior to the composition of the invention. Thus, the composition containing the NTA complexed with Sm-153 shows high liver uptake while that containing the DTPA complex has low skeletal uptake.

Comparative Examples C and D

Compositions containing complexes of Sm-153 with HEEDTA or EDTA were prepared with L/M molar ratios of 10:1 and 5:1 respectively*. The compositions containing the Sm-153-HEEDTA and Sm-153-EDTA are indicated as Examples C and D, respectively, and are shown along with Examples 1 and 5 in Table III, for comparison. Note that the liver uptake in the lower molar ratios of L/M is about 2 to about 5 times that of the higher molar ratios, thus demonstrating that compositions with low L/M molar ratio are undesirable.

*These are the molar ratios employed in the O'Mara, et. al. and Rosoff, et. al. references previously cited.

TABLE III

| Example No. | Complex L/M | Ratio L/M | Time (Hrs) | Percent of Injected Dose in | |
| --- | --- | --- | --- | --- | --- |
|  |  |  |  | Liver | Bone |
| 1 | Sm-153/HEEDTA | 300/1 | 2 | 2.4 | 58 |
| C | Sm-153/HEEDTA | 10/1 | 3 | 11.7 | 38 |
| 5 | Sm-153/EDTA | 300/1 | 2 | 4.4 | 43 |
| D | Sm-153/EDTA | 5/1 | 2 | 8.0 | 50 |

*These are the molar ratios employed in the O'Mara, et. al. and Rosoff, et. al. references previously cited.

EXAMPLE 7

In another experiment Sm-153 was complexed with HEEDTA in a manner similar to that of Example 1 at L/M molar ratios of 10/1, 20/1, 50/1, 100/1, 200/1 and 300/1. The compositions so formed at the various L/M molar ratios were injected into rats as in the preceding examples. the percentage of the injected dose which localized in liver and bone was determined two hours after the injection. Results are shown in Table IV.

TABLE IV

| Molar Ratio (L/M) | Percent of Injected Dose in | |
| --- | --- | --- |
|  | Liver | Bone |
| 10/1 | 12.8 | 34 |
| 20/1 | 6.3 | 51 |
| 50/1 | 5.1 | 55 |
| 100/1 | 1.7 | 49 |
| 200/1 | 1.0 | 46 |
| 300/1 | 0.5 | 49 |

EXAMPLE 8

In the manner of Example 6, Ho-166 was complexed with HEEDTA at L/M molar ratios of 10/1, 50/1 and 300/1. Again, each of these compositions was injected into rats and the percent present in various tissues and bone determined at two hours after injection. Results are shown in Table V.

TABLE V

| Percent of Injected Dose in | 10/1 | 50/1 | 300/1 |
| --- | --- | --- | --- |
| Liver | 2.9 | 0.7 | 0.4 |
| Blood | 0.6 | 0.5 | 0.1 |
| Muscle | 3.6 | 2.3 | 1.8 |
| Bone | 52 | 56 | 66 |
| Bone/Liver | 9 | 44 | 92 |
| Bone/Blood | 64 | 88 | 502 |
| Bone/Muscle | 72 | 122 | 189 |

EXAMPLE 9

A 10 year old coonhound which had been limping for about 6 weeks was radiographically determined to have a bone lesion in the right femur. The dog was non-weight bearing on the affected leg when presented for examination. A diagnostic bone scan, utilizing Tc-99 m-MDP, showed an increased uptake of the radioactivity in the mid-shaft area of the right femur. No other areas of increased uptake were observed. A composition of HEEDTA and Sm-153 at an L/M molar ratio of 300/1 prepared as in Example 1 was injected into the dog. The dose was 30.35 mCi which amounted to 1.03 mCi/kg.

Scintillation scans of the injected Sm-153 composition showed increased Sm-153 uptake similar to the diagnostic scan, thus confirming increased uptake of the Sm-153 in a clinically identified lesion.

Two weeks after treatment the dog was bearing weight on the right rear leg and after three weeks appeared to be using the leg 80-90% of the time.

EXAMPLE 10

A quantity of 25 mg of hydroxyethlethylenediaminetriacetic acid (HEEDTA) was dissolved in one ml of water. NaOH was added to affect dissolution and to raise the pH to approximately 7.4. The final concentration of HEEDTA in the solution was $8.99 \times 10^{-2}$M (Solution No. 1). A quantity of 16.7 microliters of the aforementioned solution was added to one ml of a Sm-153 solution which was $3 \times 10^{-4}$M samarium and 0.1M HCl. The molar ratio of HEEDTA to samarium was 5:1. The pH of this solution was adjusted to 7.4. Male Sprague-Dawley rats weighing about 150-200 grams were injected first with 100 microliters of the HEEDTA solution (Solution No. 1) via the tail vein. Immediately following the injection of the HEEDTA solution, 100 microliters of the Samarium-153-HEEDTA solution was injected via the tail vein. The animals were sacrificed 2 hours after injection and the biodistribution of the Sm-153 determined

TABLE VI

|            | Rat 1 | Rat 2 |
|------------|-------|-------|
| Weight (g) | 153   | 162   |
| Bone (%)   | 62    | 44    |
| Liver (%)  | 0.79  | 0.89  |
| Spleen (%) | 0.009 | 0.007 |
| Muscle (%) | 2.54  | 0.33  |
| Blood (%)  | 0.14  | 0.08  |

We Claim:

1. A composition comprising a complex which comprises a chelant and a radionuclide wherein the chelant is hydroxyethylethylenediaminetriacetic acid or a physiologically acceptable salt thereof with a radionuclide selected from the group consisting of Sm-153, Gd-159 and Ho-166, wherein the molar ratio of chelant to radionuclide is about 50:1 or more, and a physiologically acceptable liquid carrier.

2. The composition of claim 1 wherein the complex is hydroxyethylethylenediaminetriacetic acid with Sm-153.

3. The composition of claim 1 wherein the complex is hydroxyethylethylenediaminetriacetic acid with Gd-159.

4. The composition of claim 1 wherein the complex is hydroxyethylethylenediaminetriacetic acid with Ho-166.

5. The composition of claim 1 wherein the chelant is at least partially in the form of its physiologically acceptable salt.

6. The composition of claim 5 wherein the physiologically acceptable salt is at least partially in the form of its alkali or alkaline earth metal salt.

7. A method for the therapeutic treatment of an animal having one or more calcific tumors which comprises administering to said animal a therapeutically effective amount of a composition comprising a complex which comprises a chelant and a radionuclide wherein the chelant is hydroxyethylethylenediaminetriacetic acid or a physiologically acceptable salt thereof with a radionuclide selected from the group consisting of Sm-153, Gd-159 and Ho-166, wherein the molar ratio of chelant to radionuclide is about 50:1 or more, and a physiologically acceptable liquid carrier.

8. The method of claim 7 wherein the complex is hydroxyethylethylenediaminetriacetic acid with Sm-153.

9. The method of claim 7 wherein the complex is hydroxyethylethylenediaminetriacetic acid with Gd-159.

10. The method of claim 7 wherein the complex is hydroxyethylethylenediaminetriacetic acid with Ho-166.

11. The method of claim 7 wherein the chelant is at least partially in the form of its physiologically acceptable salt.

12. The method of claim 11 wherein the physiologically acceptable salt is at least partially in the form of its alkali or alkaline earth metal salt.

13. A method for the therapeutic treatment of an animal having bone pain which comprises administering to said animal a theerapeutically effective amount of a composition comprising a complex which comprises a chelant and a radionuclide wherein the chelant is hydroxyethylethylenediaminetriacetic acid or a physiologically acceptable salt thereof with a radionuclide selected from the group consisting of Sm-153, Gd-159 and Ho-166, wherein the molar ratio of chelant to radionuclide is about 50:1 or more, and a physiologically acceptable liquid carrier.

14. The method of claim 13 wherein the complex is hydroxyethylethylenediaminetriacetic acid with Sm-153.

15. The method of claim 13 wherein the complex is hydroxyethylethylenediaminetriacetic acid with Gd-159.

16. The method of claim 13 wherein the complex is hydroxyethylethylenediaminetriacetic acid with Ho-166.

17. The method of claim 13 wherein the chelant is at least partially in the form of its physiologically acceptable salt.

18. The method of claim 17 wherein the physiologically acceptable salt is at least partially in the form of its alkali or alkaline earth metal salt.

* * * * *

UNITED STATES PATENT AND TRADEMARK OFFICE
CERTIFICATE OF CORRECTION

PATENT NO. : 4,897,254

DATED : January 30, 1990

INVENTOR(S) : Jaime Simon, et al.

Page 1 of 2

It is certified that error appears in the above-identified patent and that said Letters Patent is hereby corrected as shown below:

On the front page, under "OTHER PUBLICATIONS", 2 references are missing. They read -- Rosoff et al., International Journal Applied Radiation. Isotope, Vol 14, pp. 129-135 (1963). O'Mara et al., Journal Nuclear Medicine, Vol. 10(1), pp. 49-51 (1969) -- .

On the front page, under "OTHER PUBLICATIONS", "Chemical Abstract 912:97498h." should read -- Chemical Abstract 91:97498h. -- .

Column 3, line 13, "or" should read -- of -- .

Column 4, line 6, "*Metallon*" should read -- *Metal-Ion* -- .

Column 6, line 22, "sifficient" should read -- sufficient -- .

Column 6, line 49, "liquid" should read -- ligand -- .

Column 7, line 22, "radinuclide" should read -- radionuclide -- .

Column 8, line 36, "inthe" should read -- in the -- .

Column 9, line 4, "H1-166" should read -- Ho-166 -- .

Column 9, line 37, "diethyleneriaminepentaacetic" should read -- diethylenetriaminepentaacetic -- .

Column 9, line 52, "composition" should read -- compositions -- .

Column 11, line 25, "hydroxyethlethylenediaminetriacetic" should read -- hydroxyethylethylenediaminetriacetic -- .

UNITED STATES PATENT AND TRADEMARK OFFICE
CERTIFICATE OF CORRECTION

PATENT NO. : 4,897,254

DATED : January 30, 1990

INVENTOR(S) : Jaime Simon et al.

It is certified that error appears in the above-identified patent and that said Letters Patent is hereby corrected as shown below:

Column 12, line 41, "theerapeuttically" should read -- therapeutically -- .

Signed and Sealed this

Twenty-sixth Day of March, 1991

Attest:

HARRY F. MANBECK, JR.

*Attesting Officer*      *Commissioner of Patents and Trademarks*